United States Patent [19]

Toglia et al.

[11] 4,155,352
[45] May 22, 1979

[54] NYSTAGMUS PROCESSOR FOR EEG MACHINES

[75] Inventors: Joseph U. Toglia, Ardmore; Charles M. Philips, Philadelphia, both of Pa.

[73] Assignee: Temple University, Philadelphia, Pa.

[21] Appl. No.: 804,879

[22] Filed: Jun. 9, 1977

[51] Int. Cl.$^2$ ............................................. A61B 5/05
[52] U.S. Cl. .................................... 128/733; 128/745
[58] Field of Search .................. 128/2 N, 2 T, 2.1 R, 128/2.1 B, 2.1 M, 2.1 P, 2.06 B, 2.06 A

[56] References Cited

U.S. PATENT DOCUMENTS

| | | | |
|---|---|---|---|
| 3,774,593 | 11/1973 | Hakata et al. | 128/2.1 M X |
| 3,794,017 | 2/1974 | Servos | 128/2.1 M |
| 3,811,428 | 5/1974 | Van Horn et al. | 128/2.06 B X |
| 3,858,034 | 12/1974 | Anderson | 128/2.06 A X |
| 3,905,355 | 9/1975 | Brudny | 128/2.1 M |
| 3,924,606 | 12/1975 | Silva et al. | 128/2.1 B |

FOREIGN PATENT DOCUMENTS 1288398  9/1972  United Kingdom ..................... 128/2 N

OTHER PUBLICATIONS

Roby, R. J., et al., "A Simplified Circuit for Stimulus-Artifact Suppression," EEG and Clin-Neurophys., v. 39, No. 1, pp. 85–877/75.

Ray, C. D., "Medical Engineering: Quantitative B, Techniques in EEG," Yearbook Publishers, Chicago 1974, p. 391.

Smith, D. A., "Medical Electronics Handbook," Howard Sons & Co., N. Y., 1962, pp. 119–120.

Huntsman, L. L. et al., "A Low-Cost Hi-Gain Amplifier with Exceptional Noise Performance," IEEE Transactions on Biomed Engr., v. 18, #4, Jul. 1971, pp. 301–302.

"Mind Power: Alpha," Radio-Electronics, v. 47, No. 7, pp. 36–39, 91, Jul. 1976.

Grieco, A. et al., "A New Apparatus for the Simultaneous Quantitative Evaluation of Several Biological Signals Relevant to Work Physiology," Med. & Biol. Engr., 1971, v. 9, pp. 705–710.

Primary Examiner—Robert W. Michell
Assistant Examiner—Francis J. Jaworski

[57] ABSTRACT

A pair of active probes and a datum probe are affixed to the patient, and the active probes' signals are coupled to a preamplifier involving both common mode rejection and differential amplification. The information bearing voltage levels are coupled to a voltage controlled oscillator, the output of which bears information in the form of frequency variations. A photocoupler isolates the patient from unwanted feedback, and drives a phase locked loop which demodulates the signal back to an information bearing voltage. The derivative of the voltage signal is taken, is separated by polarity to correspond to the direction of eye motion, and is coupled to the EEG, thereby representing nystagmus velocity.

3 Claims, 4 Drawing Figures

NYSTAGMUS PROCESSOR FOR EEG MACHINES

BACKGROUND OF THE INVENTION

This invention relates to clinical observation and recording of eye motion and velocity, and more particularly to apparatus and methods for adapting conventional electroencephalograph (EEG) machines to record nystagmus.

Nystagmus is the involuntary, rhythmic motion of the eye caused by certain pathological conditions. Studies of nystagmus have indicated certain qualitative and quantitative factors are adequately clinically characteristic of nystagmus. For example, with respect to spontaneous nystagmus, the qualitative parameters include eye direction, rhythm, and form, and the quantitative parameters include amplitude, frequency and speed. Further, the clinical utility of observing nystagmus extends not only to the recording and study of spontaneous nystagmus, but also of induced nystagmus induced by caloric, rotary, and the like stimuli. Such induced nystagmus may be characterized by further significant clinical parameters, such as total amplitude, total number of beats, and duration.

Increasingly, the recording and study of significant parameters relating to spontaneous and induced nystagmus is being utilized as a diagnostic aid. Moreover, such utility is being found not only by specialists dealing with the eyes and proximately related areas, but also in the fields of neurology and otology. That is, it has been found that the parameters associated with spontaneous and induced nystagmus are linked to pathological factors of considerable clinical variety, including for example neck whiplash injuries, diverse injuries of the brain and skull, otological maladies, and the like.

Accordingly, the measurement and study of nystagmus is a clinical tool of widespread utility. Historically, nystagmography has evolved technically utilizing various arts. Early on, mechanical systems of levers and the like were utilized, but successful developments have tended to revolve around optical and electrical methods, and such are the techniques conventionally used today.

The electrical methods, commonly known as electronystagmography (ENG), are based on the proposition that the eyeball is charged, and behaves as an electrical dipole. Motion of the eyeball produces a varying voltage on the surrounding skin, which is nearly proportional to the position of the eye. Accordingly, electrodes may be placed in electrical contact with that skin area, sensing voltage changes and thereby producing an electrical signal representative of the eye motion. Such electrical signals correspond quite accurately to the critical clinical parameters relating to nystagmus. An extensive exposition of electronystagmography, including its technical and clinical aspects, and an index of neurological, otological, and ophthalmological cases, may be found in "*Electronystagmography-Technical Aspects and Atlas*" by Joseph U. Toglia, M.D., C.C. Thomas, Springfield, Illinois (1976).

Perhaps the greatest limitation to the continuing increase of clinical use, and development of further clinical methods and applications of electronystagmography, is the considerable expense associated with acquisition of ENG machines. Hence, the simple economics of machine cost versus expected frequency of use tend to dictate which practitioners and/or hospitals acquire ENG machinery. More often than not, practitioners who sometimes would find ENG analysis to be quite clinically useful, cannot justify the expense of acquiring an ENG recorder simply because of the relative infrequency of such occasions. This is particularly true for practitioners such as neurologists.

It is a primary object of the present invention to provide relatively inexpensive ENG apparatus whereby electronystagmographic diagnostic techniques may be economically extended to many practitioners who cannot presently justify the expense of ENG machinery.

While the incidence of ENG machinery is relatively uncommon with respect to the number of practitioners who might find them useful, the incidence of EEG machines is considerably greater. Further, EEG machines constitute a virtually essential tool of many practitioners for whom ENG machines are a useful but economically unjustified facility.

It is a primary object of the present invention to provide apparatus and methods for adapting EEG recorders to perform the ENG functions.

It is a further object of the present invention that the apparatus affording such adaptation function be compact and inexpensive, whereby EEG machines may be unobtrusively and conveniently adapted to record ENG functions.

It is a still further object that the adaptation apparatus in accordance with the present invention function in conjunction with conventional EEG machines on essentially a "black box" basis, whereby the adapter unit simply plugs into the input of the conventional EEG recorder, and utilizes conventional probe electrodes on the patient.

In accordance with yet another object of the present invention, it is essential that the patient be at all times protected from the electrical potentials and signals utilized in the ENG/EEG process, not only to avoid dangers from electrical shock and the like, but also to avoid spurious feedback signals which would impair the accuracy of the ENG record.

SUMMARY OF THE INVENTION

The present invention involves as interface unit whereby conventionally located electrodes for sensing nystagmus produce signals which are processed and then coupled directly to EEG recorder inputs. The corresponding record contains relevant information as though recorded on an ENG unit. Basically, three major segments are involved, including a preamplifier, an isolator, and a derivative-polarity selector section. The preamplifier section, which operates directly in response to voltage signals conveyed from the probe, not only provides suitable overall gain for the eye motion signal, but also employs a pair of followers, respectively responsive to different electrode probe signals, which operate differentially with respect to a common to reject interference. The preamplifier also converts the dual probe signal into a single ended signal. The isolator segment separates the subject from the remaining apparatus, thereby preventing both power (i.e., safety) and signal (i.e., feedback) of the subsequent circuitry from being coupled back to the subject. The derivative-rectifier section develops representations of eye velocity during nystagmus, and separates right-going and left-going velocities from one another based on their respective polarities. The eye motion as well as the eye velocity signals are coupled directly to the EEG recorder inputs, and thereby are recorded as though in an ENG machine.

DETAILED DESCRIPTION

Figure 1:
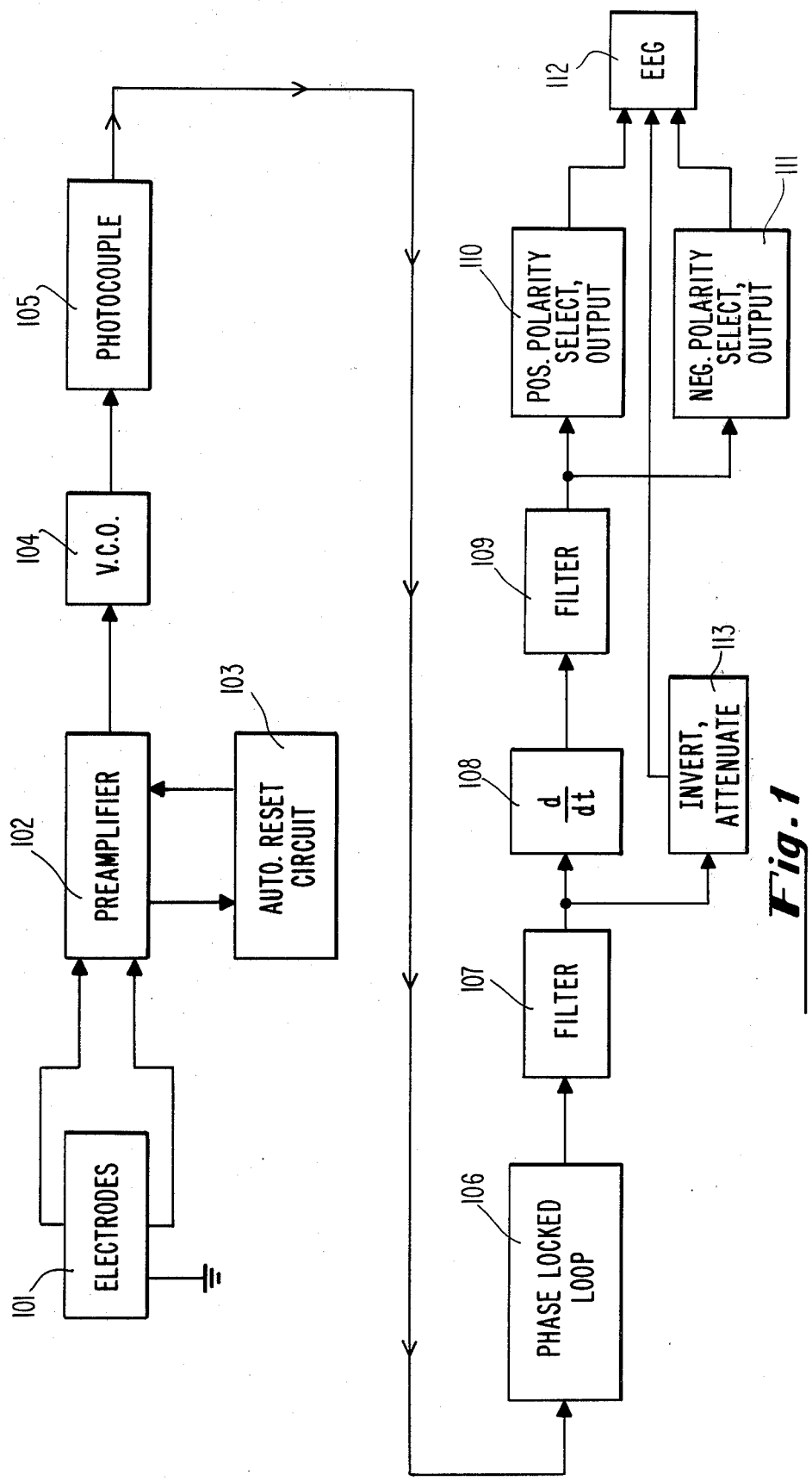
FIG. 1 shows a block diagrammatic representation of a preferred embodiment of the present invention.

Referring first to FIG. 1, there is shown a block diagrammatic representation of a preferred embodiment of the present invention. It will be appreciated that the embodiment of FIG. 1 comprises functional blocks largely conventional in accordance with the knowledge of those of ordinary skill in the art. Nevertheless, a preferred schematic version thereof is presented in FIGS. 2a through 2c, employing commercially available components. It is to be understood that numerous such schematics will readily occur to those of ordinary skill in the art to embody the block diagrammatic representation of FIG. 1. It will be further understood that although FIG. 1 sets forth a preferred embodiment in block diagrammatic form, numerous alternative schemes will occur to those of ordinary skill in the art without departure from the spirit or scope of the present invention, as defined by the appended claims.

In FIG. 1, the electrodes 101 are applied to the face of the patient in conventional fashion, and at positions well established in the art. See the above referenced text of J. U. Toglia. For purposes of the instant application for a given patient, three electrodes are depicted, two "active" probes, one at the corner of each eye, and one "ground" probe, connected to the patient at a point disparate from the eyes.

The probe signals are coupled to a preamplifier section 102, which in turn, employs an automatic reset circuit 103. The preamplifier section 102 functions to convert the double-ended signal from the two active electrodes from 101 into a single-ended signal (i.e., having respective polar extremities corresponding to the directional extremes of eye positions), and also provides the desired amount of gain for the remainder of the system. The automatic reset circuit 103 is active when the FIG. 1 system is first energized, and regulates the charge on coupling capacitors in the preamplifier 102, thereby preventing transients associated with electrode placement from overloading the FIG. 1 system or saturating components thereof. After a predetermined length of time, the automatic reset circuit cuts itself out from the system, and the preamplifier 102 thereafter operates in response to signals from the electrodes 101. The signal at the output of preamplifier 102 therefore employs voltage levels representative of the eye position, as sensed by the active electrodes of 101.

The voltage signal from the preamplifier 102 drives a voltage controlled oscillator 104, which functions in conventional fashion to produce a signal having a frequency representative of the voltage at its input. Hence, at the output of voltage controlled oscillator 104, there is produced a pulse signal whose frequency, above and below a predetermined rest frequency, represents the analog voltage signal from preamplifier 102.

The frequency modulated signal is delivered to a photoisolator 105, embodied as a commercially available photocouple, which interrupts the path between the patient at electrode 101, and the EEG unit 112. As is known in the art, the photocouple 105 conveys the frequency signals from a light source (e.g., a light emitting diode) energized by the oscillator 104, to a photosensor which detects emissions from the light emitting diode, translating the signals back into electrical energy. Hence, the output of the photocouple 105 is a voltage scaled replica of the signal from the oscillator 104. Signals may not be translated by photocouple 105 in the inverse direction, however, thereby protecting the patient from the EEG machine power, and also preventing spurious signals from interfering in detrimental feedback fashion with the operation of the electrodes 101, preamplifier 102, and oscillator 104.

It should be understood that the isolated front end has a separate, isolated power supply, and that the "ground" connections (up to and including the input of the isolator 105), are not common to those of the output stage of isolator 105, or the succeeding circuitry of FIG. 1.

The signal from the photocouple 105, which still bears information in the form of frequency variations, is decoded back to an analog voltage signal at a phase locked loop 106. As is known in the art, phase locked loops conventionally involve a phase comparator and filter which establish an analog voltage in response to phase (frequency) differences between a first comparator input signal and a signal generated from a local voltage controlled oscillator. That oscillator output in turn is corrected by the analog voltage from the phase comparator and filter. Accordingly, in FIG. 1, the signal from the photocouple 105 is utilized as one signal for comparison at the input of the phase comparator of loop 106, and the decode voltage signal at the output of the phase comparator of loop 106 again represents the eye motion signal, in similar fashion to the output of preamplifier 102.

As desired, extra filtering may be provided at 107 in order to remove undesired noise which may have been introduced in the frequency coding-phototransmission processes at 104, 105, and 106. Accordingly, at the output of filter 107, there is presented a signal representative of eye position, and having voltage variations representative of eye motion. This signal may be coupled to the ENG machine and recorded, as indicated at 113 (employing appropriate inversion and attenuation functions). In order to determine important parameters relating to the velocity of nystagmus, however, further processing is required.

The eye position and motion signal from the filter 107 is coupled to a differentiation circuit 108 which develops the time rate of change of the eye motion signal. Since the preamplifier 102 converted the respective signal from the active electrodes 101 to a single-ended signal, and in view of the conventional utilization and placement of those electrodes, positive going voltages represent eye motions in one direction, relatively constant voltages represent the eye in a stationary position, and negative going voltage excursions represent eye motion in the opposite direction. Hence, the derivative of the eye motion signal as developed at 108 represents velocity of eye motion, with positive and negative excursions of the derivative signal respectively representing eye velocity in one direction and then the other.

A filter at 109 cleans unwanted noise from the derivative signal, and thereby presents at its output the velocity signal. For clinical application, it is useful to have eye velocity in one direction depicted separately from eye velocity in the other, and to this end, polarity selectors 110 and 111 separate left-going and right-going velocity signals from one another for separate recording at the EEG 112. The polarity selectors 110 and 111 essentially constitute rectifiers of opposite polarity to one another, and each includes suitable amplification-/attenuation output stages which insure that the signals presented to the EEG 112 are of the proper amplitude and level.

In partial summary, the embodiment of FIG. 1 involves sensing nystagmus utilizing probes sensitive to positional changes of the eye dipole, combining and amplifying those signals into a suitable single-ended signal representative of eye position, passing the signal through a unidirectional isolation stage, evaluating eye velocity (i.e., evaluating the derivative of the eye motion signal), and separating the velocity in terms of direction of eye motion. Eye position and motion, and the respective right-going and left-going velocity signals, are recorded by the EEG machine.

Figure 2A:
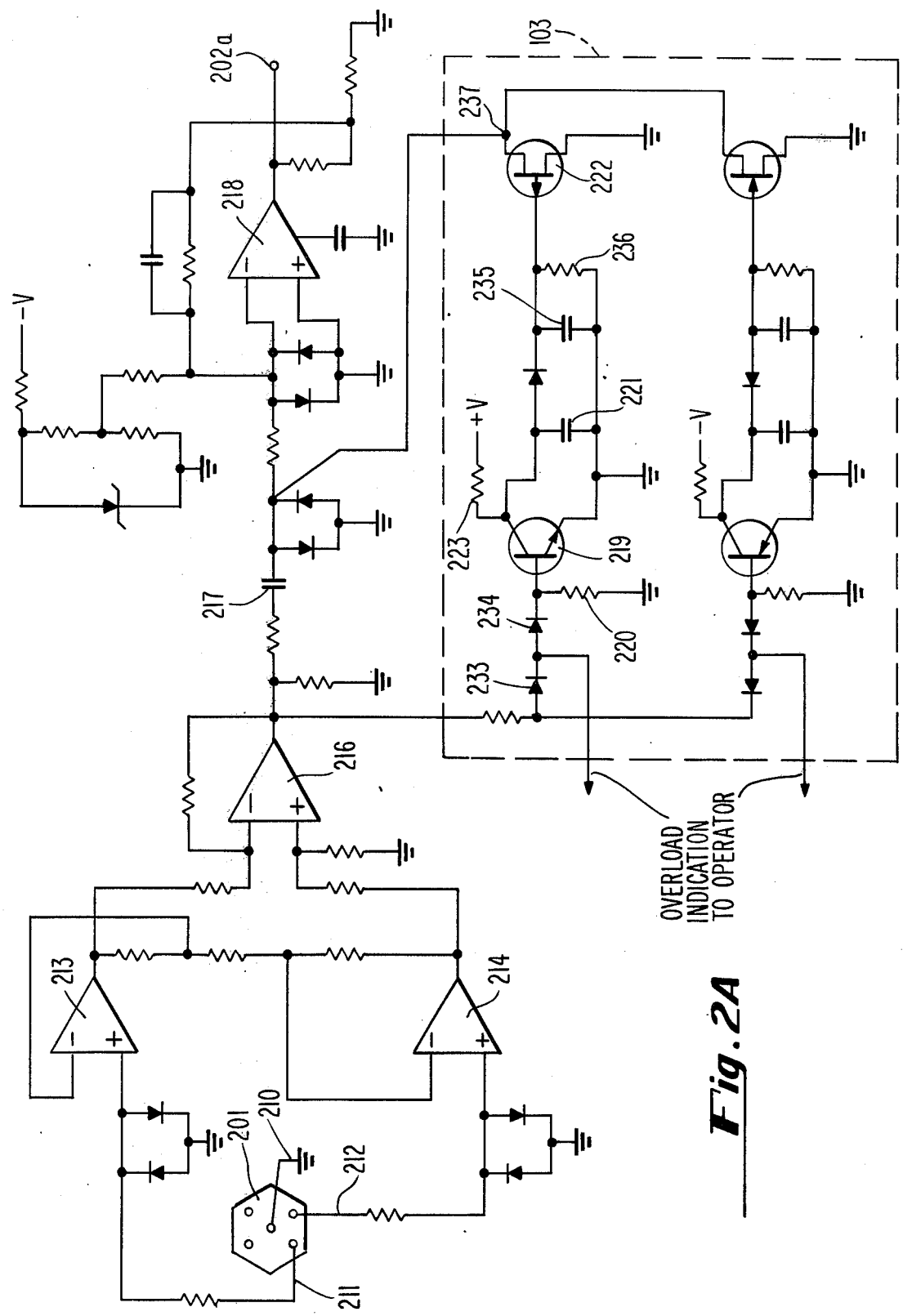
FIGS. 2a through 2c show a preferred schematic representation of the FIG. 1 embodiment.
Figure 2B:
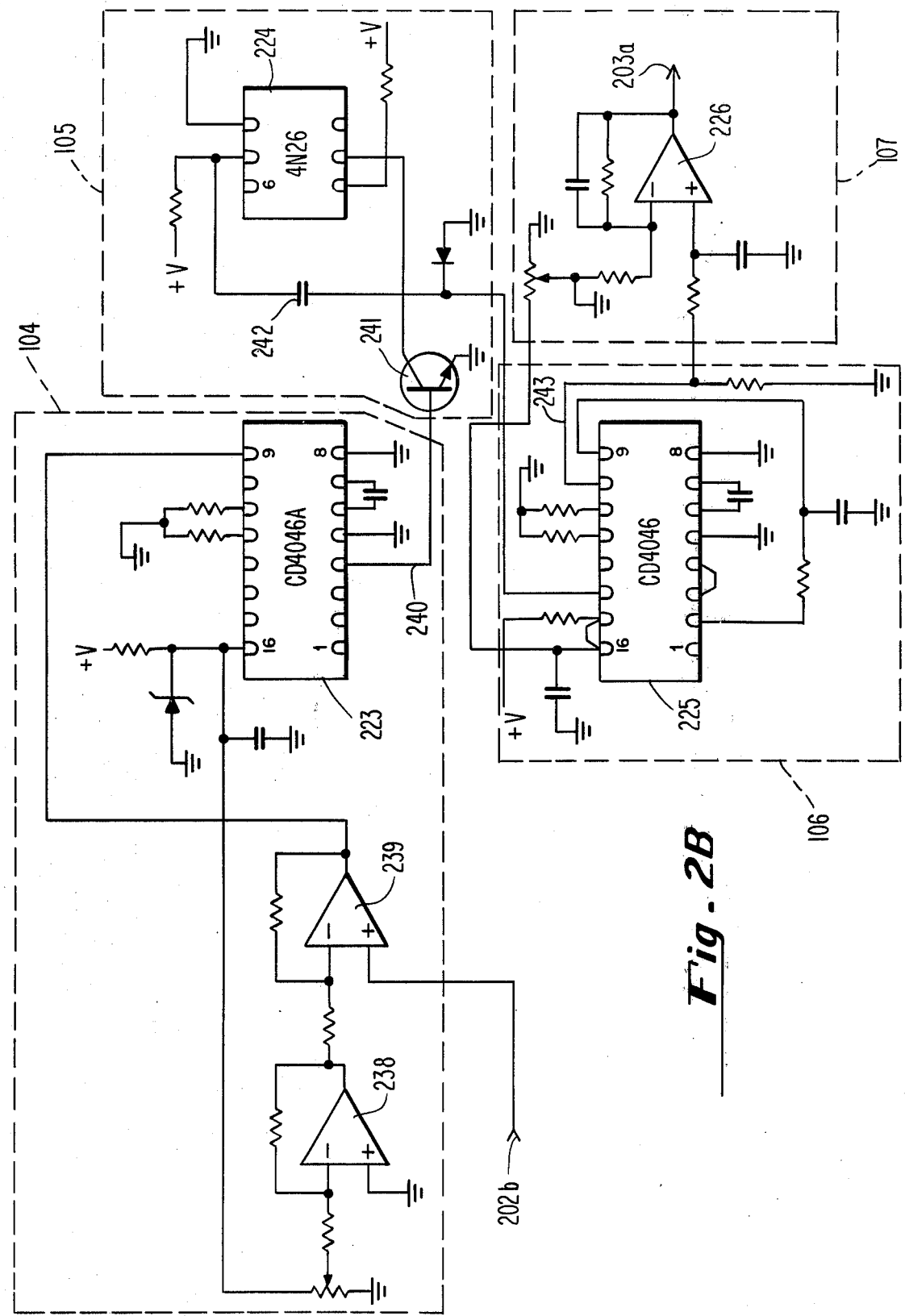
Figure 2C:
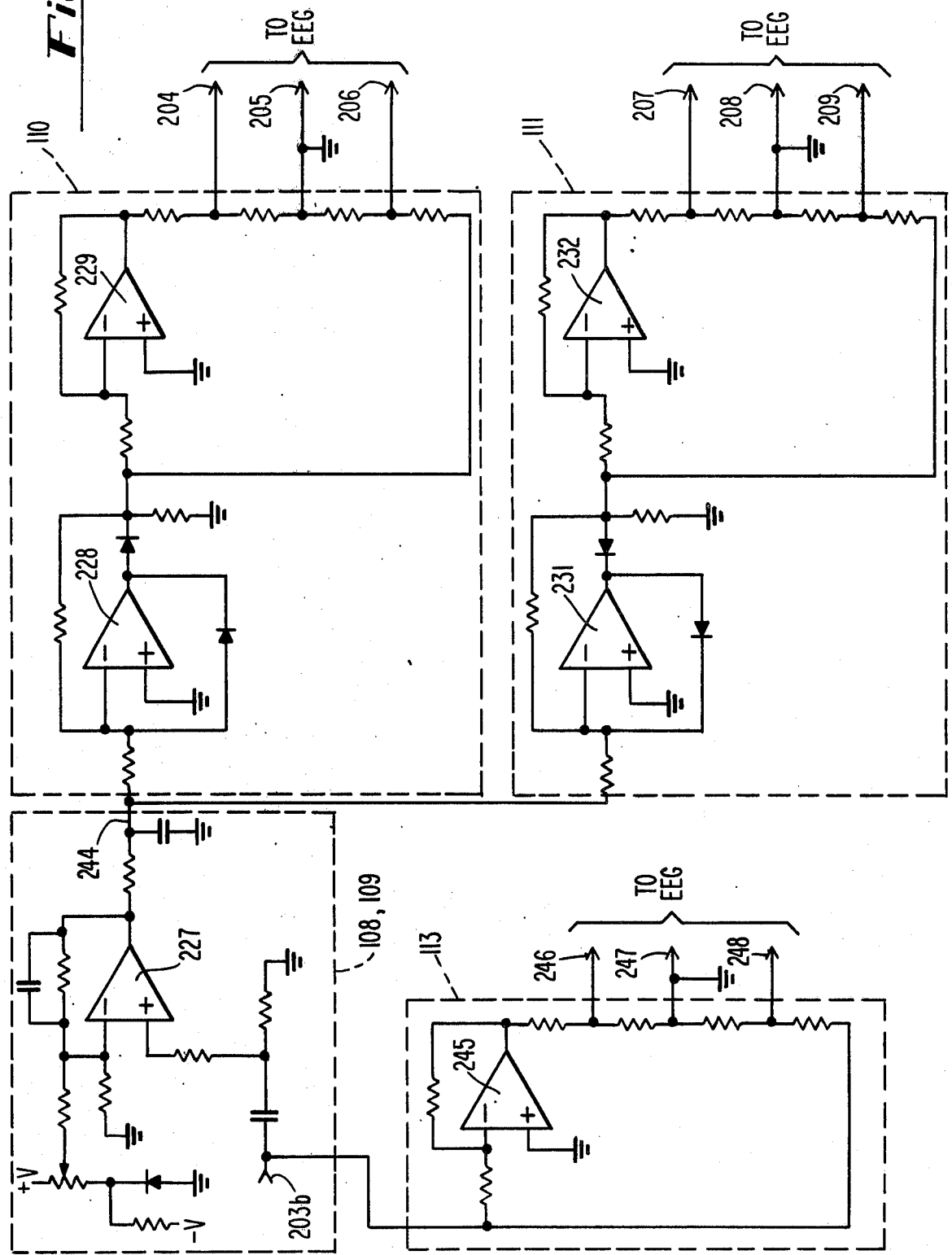

FIGS. 2a through 2c set forth a schematic diagram of a preferred embodiment of the FIG. 1 block diagram. In particular, FIGS. 2a and 2b sequentially interconnect at terminals 202a and 202b, and FIGS. 2b and 2c sequentially interconnect at terminals 203a and 203b. Signals from the electrodes are received at an input jack 201 of FIG. 2a, and terminals 204 through 209 and 246 through 248 of FIG. 2c are coupled to the input of an EEG machine. In FIG. 2a, the automatic reset circuit 103 is indicated by a broken lined enclosure; the remainder of the apparatus of FIG. 2a essentially embodies the preamplifier unit 102 of FIG. 1. In FIG. 2b, the voltage controlled oscillator 104, photocouple 105, phase locked loop 106, and filter 107 are indicated by broken lined enclosure, and in FIG. 2c, the combined derivative signal 108 and filter 109, the positive polarity selector 110, the negative polarity selector 111, and the eye position signal inverter-attenuator 113 are likewise shown.

In FIG. 2a, the voltages from the electrodes at the corner of each eye are connected via 211 and 212 to a pair of followers 213 and 214, which provide a predetermined amount of gain (e.g., 101) for the voltage between terminals 211 and 212. Gain is unity for voltage between the common electrode 210 and each of the other electrodes 211 and 212. Hence, 60 Hz interference is rejected one hundred fold.

The double-ended signals from followers 213 and 214 are respectively coupled to the inputs of a unity gain amplifier 216, which converts the double-ended signals to a single ended signal. Its rejection of a signal common to both leads is determined by the input resistor match, and is typically 100 for 1 percent resistors.

The embodiment of FIG. 2a employs AC coupling between the unity gain amplifier 216 and the final preamplifier gain stage 218, via a capacitor 217. In preferred embodiments, the final gain stage 218 employs a gain of 5. The use of AC coupling at capacitor 217 incorporates, however, the possibility of producing large transients upon attachment or disconnection of the electrodes with the machine power on, which would tend to saturate the amplifier 218. In order to avoid this possibility, the automatic reset circuit 103 is employed, which insures automatic stablization by quickly discharging capacitor 217 during overload (i.e., heavy transient) conditions.

In FIG. 2a, the stablization circuit 103 utilizes duplicate alternative paths, different from one another only in polarity of active devices and source voltages. Hence, the alternative paths of circuit 103 respectively respond to overload signals of opposite polarities. One such path shall herein be discussed in detail, it being understood that the alternative path functions identically for overload signals of opposite polarity. Diodes 233 and 234, in conjunction with resistor 220 and transistor 219, comprise a threshold circuit, energized when the output from amplifier 216 exceeds a predetermined voltage representative of overload (e.g., 2 volts). Exceeding this threshold switches transistor 219 to an "on" condition, thereby discharging capacitor 221. Junction field effect transistor 222 is normally in a non-conducting state, but the discharging operation of transistor 219 on capacitor 221 (and thereby also on the RC combination 235 and 236 after a short discharging time delay) energizes junction field effect transistor 222, dropping the potential of its drain terminal 237 substantially to ground. Capacitor 217 is then quickly charged by amplifier 216. When the overload condition subsides, transistor 219 is disabled, and capacitors 221 and 235 are charged via resistor 223. Thereupon, junction field effect transistor 222 once more is switched off, its drain potential at 237 is released from ground, and capacitor 217 is conditioned for operation as an AC couple between amplifiers 216 and 218.

The preponderance of apparatus shown in FIG. 2b constitutes an isolator between the patient and the EEG machine. The preamplified signal is delivered at terminal 202b to the voltage controlled oscillator 104, the primary component of which is an integrated circuit module commercially available under the trade designation "CD 4046A". A pair of amplifiers 238 and 239 provide level shift and scaling operations to the preamplifier output, and couple the signal to the input (pin 9) of the integrated circuit oscillator 223. The oscillator 223 produces an output pulse signal, the frequency of which varies up and down from a predetermined center frequency as the analog voltage at terminal 202b correspondingly varies up and down from a mean value. Hence, the signal at 240 may be regarded as a frequency modulated version of the analog voltage at terminal 202b.

The signal at output terminal 240 of oscillator 223 drives a transistor 241, which in turn operates a light emitting diode in the input stage of integrated circuit 224. As shown, integrated circuit 224 constitutes a unit commercially available under the trade designation "4N26", which includes a light emitting diode (LED) input stage, and a phototransistor output stage. The LED and the phototransistor are optically coupled within integrated circuit 224, and the phototransistor output is AC coupled via a capacitor 242 to the input of the phase locked loop 106.

As shown, the phase locked loop 106 largely consists of an integrated circuit 225 designated "CD 4046", with ancillary biasing and interconnection circuitry. The output terminal 243 of integraged circuit 225 represents the demodulated FM signal, that is, an analog voltage corresponding to the signal coupled to the oscillator 104 at input terminal 202b.

The frequency modulation at 104, photocoupling at 105, and demodulation at 106 interrupts the path from the EEG machine power so that no path allows for that power to be conveyed back to the patient. If the EEG machine ground were attached to the patient and the ground wire broke, leakage current from the EEG machine, often in the range of 50 to 100 micro-amperes, could flow through the patient if he touched a grounded object. The configuration shown eliminates such possibility. Similarly, the isolation provided allows for safe attachment of ancillary apparatus (e.g., magnetic tape recording systems) at the output terminal 243 of the phase locked loop 106.

The demodulated FM signal at 243 is filtered at amplifier 226 to remove carrier ripple, and the filtered signal is coupled via 203a and 203b to the differentiator 108. As shown in FIG. 2c, the functions of the differentiator 108 and following filter 109 are incorporated into the circuitry associated with amplifier 227, the filtering function occurring in the feedback circuitry of amplifier 227, and in the RC network following amplifier 227. Hence, the differentiated signal at 244 is essentially free of spurious signals, such as noise.

The right-going and left-going eye motion velocities from 244 are separated by rectifiers respectively comprising amplifiers 228 and 231, which are of opposite operational polarity to one another. These signals are respectively converted to differential signals by inversion at amplifiers 229 and 232, and each is attenuated by series resistors to be suitable as a direct machine input to conventional EEG recorders. Hence, the left-going eye velocity signal is coupled to the EEG at output terminals 204, 205, and 206, and the right-going eye velocity signal is coupled to the EEG via output terminals 207, 208, and 209. In accordance with conventional practice, phone tip jacks are utilized at EEG inputs from scalp electrodes. The outputs 204 through 206, and 207 through 209 may each be embodied as suitably color coded three pair shielded cable, terminating in phone tip plugs, thereby enabling use of the apparatus in conventional fashion by anyone familiar with EEG operation.

The eye motion signal itself, from terminal 203b and prior to differentiation, is representative of eye position and motion, and is therefore also useful. Amplifier 245 employs a configuration similar to amplifiers 229 and 232, and functions to invert and attenuate the eye position/motion signal from filter 107, for EEG input in similar fashion to that accomplished for the eye velocity signals at 110 and 111.

In summary, the embodiment of FIGS. 2a through 2c sets forth a preferred configuration wherein conventional electrodes are applied to the patient and coupled to a nystagmus processor circuit, the output of which at 204 through 206, 207 through 209, and 246 through 248 is coupled directly and in conventional fashion to any EEG machine. The EEG recorders will register eye motion, left-going eye velocity, and right-going eye velocity in response thereto. It is to be understood, however, that numerous alternative embodiments will occur to those of ordinary skill in the art without departure from the spirit or scope of the present invention.

We claim:

1. Interface apparatus for adapting an electroencephalograph (EEG), having an input including a positive, a negative and a ground connection; to perform electronystagmograph (ENG) functions, comprising:

a plurality of probes locatable at predetermined positions on a patient, said probe plurality including two active probes and a datum probe, said active probes each being capable of independently detecting a voltage signal relative to said datum probe;

means, associated with said probe plurality, for converting said voltage signal detected by each of said two active probes into a single voltage coded signal being the difference of said two signals detected, wherein said converting means includes means for differentially amplifying signals from said two active probes, being connected to each of said active probes, and means for providing a frequency modulated isolation of said difference amplifying means output, being connected thereto;

wherein said converting means includes a differential amplifier connected at its inputs to said two active probes, and an amplitude operated start-up transient signal suppressor circuit associated with said differential amplifier;

means for providing a first order time differential of said coded difference signal, said time differential means being connected to said converting means;

means for separating said time differential signal into a positive polarity component and a negative polarity component, said components each being conveyed by a positive and negative connection pair, said connection pair capable of being connected to the positive and negative inputs of said electroencephalograph (EEG); and means for reconverting the output of said frequency modulated oscillator means into two separate signals each being proportional to one of said signals detected by said active probes, said reconverting means capable of being connected for connecting said frequency modulated isolator means to respective positive and negative inputs of said electroencephalograph (EEG);

wherein said first order time differential means includes a differentiator circuit:

wherein said reconverting means includes a first filter connected to said differentiator circuit output; and a pair of opposite polarity selectors connected in parallel to said first filter output; and wherein said apparatus also includes means for modulating a voltage signal, said modulation means being driven by the output of said differential amplifier; an isolator connected to the output of said modulation means; means for demodulating a modulated signal, said demodulating means being connected to said isolator; and a second filter connected between said demodulation means and said differentiator circuit.

2. Apparatus of claim 1 wherein said pair of opposite polarity selectors each includes a rectifier associated with said differentiator circuit; and wherein said modulation means includes a voltage controlled oscillator driven by the output of said differential amplifier; wherein said isolator is a photo isolator; and wherein said demodulation means includes a phase locked loop circuit connected to said photo isolator.

3. Apparatus of claim 2 also including an inverter attenuator circuit connected to the output of said second filter.

* * * * *